United States Patent [19]

Tighe et al.

[11] Patent Number: 5,403,591
[45] Date of Patent: Apr. 4, 1995

[54] METHODS FOR INHIBITING SKIN ULCERATION BY USE OF CYANOACRYLATE ADHESIVES

[75] Inventors: Patrick J. Tighe, Littleton; Michael M. Byram; Leonard V. Barley, Jr., both of Colorado Springs, all of Colo.

[73] Assignee: Medlogic Global Corporation, Colorado Springs, Colo.

[21] Appl. No.: 82,927

[22] Filed: Jun. 25, 1993

[51] Int. Cl.$^6$ ..................... A61L 15/00; A61K 31/765
[52] U.S. Cl. ................................. 424/445; 424/78.02; 514/928
[58] Field of Search .................. 424/78.02, 78.06, 445; 514/928

[56] References Cited

U.S. PATENT DOCUMENTS

| | | | |
|---|---|---|---|
| 2,804,073 | 8/1957 | Galliene et al. | 128/156 |
| 3,527,224 | 9/1970 | Rabinowitz | 526/297 |
| 3,591,676 | 7/1971 | Hawkins et al. | 424/78.06 |
| 3,667,472 | 6/1972 | Halpern | 260/45.5 |
| 3,995,641 | 12/1976 | Kronenthal et al. | 558/400 |
| 4,035,334 | 7/1977 | Davydov et al. | 424/78.06 |
| 4,444,933 | 8/1984 | Colubmus et al. | 524/292 |
| 4,650,826 | 3/1987 | Waniczek et al. | 524/292 |
| 4,958,748 | 9/1990 | Otake | 128/156 |

OTHER PUBLICATIONS

Akers, Arch. Dermatol., vol. 107, pp. 544–547, (Apr. 1973).
Bhaskar, Surindar N. et al., "Healing of Skin Wounds with Butyl Cyanoacrylate", pp. 294–297, 1969, Journal of Dental Research, vol. 48, No. 2.
Dalvi, A. et al., "Non-suture Closure of Wound Using Cyanoacrylate", pp. 97–100, 1986, Journal of Postgraduate Medicine, vol. 32, No. 2.
Eiferman, Richard A. et al., "Antibacterial Effects of Cyanoacrylate Glue", pp. 958–960, Jun. 1983, Archives of Ophthalmology, vol. 101.
Ellis, David A. F. et al., "The Ideal Tissue Adhesive in Facial Plastic and Reconstructive Surgery", pp. 68–72, 1990, The Journal of Otolaryngology, vol. 19, No. 1.
Fung, Ramona Q. et al., "Use of Butyl-2-Cyanacrylate in Rabbit Auricular Cartilage", pp. 459–464, Jul. 1985, Archives of Otolaryngology, vol. 111.
Galil, K. A. et al., "The Healing of Hamster Skin Ulcers Treated with N-butyl-2-cyanoacrylate (Histoacryl blue)", pp. 601–607, 1984, Journal of Biomedical Materials Research, vol. 18.
Harper, Marion C., "Stabilization of Osteochondral Fragments Using Limited Placement of Cyanoacrylate in Rabbits", pp. 272–276, Jun. 1988, Clinical Orthopaedics and Related Research 231.
Kamer, Frank M. et al., "Histoacryl: Its Use in Aesthetic Facial Plastic Surgery", pp. 193–197 Feb. 1989, Archives of Otolaryngology Head and Neck Surgery, vol. 115.
Kosko, Paul I., "Upper Lid Blepharoplasty: Skin Closure Achieved with Butyl-2-Cyanoacrylate", pp. 424–425, Jun. 1981, Ophthalmic Surgery, vol. 12.
Lehman, Ralph A. W. et al., "Toxicity of Aklyl 2-Cyanoacrylate: Bacterial Growth", pp. 447–450, Sep. 1966, Archives of Surgery, vol. 93.
Leonard, Fred et al., "Synthesis and Degradation of Poly(alkyl-a-Cyanoacrylate)", pp. 259–272, 1966, Journal of Applied Polymer Science, vol. 10.
Makady, F. M. et al., "Effect of tissue adhesives and suture paterns on experimentally induced teat lacerations in lactating dairy cattle", pp. 1932–1934, Jun. 1991, Javma, Reports of Original Studies, vol. 198, No. 11.
Matsumoto, Teruo, "Bacteriology and Wound Healing", pp. 106–113, 1972, Chapter 3 in Tissue Adhesives in Surgery.
Matsumoto, Teruo, "Clinical Considerations and Applications of Bucrylate Tissue Adhesive", pp. 226–237, (List continued on next page.)

Primary Examiner—Raymond Henley, III
Attorney, Agent, or Firm—Burns, Doane, Swecker & Mathis

[57] ABSTRACT

A cyanoacrylate adhesive is applied onto surface skin areas prone to ulceration so as to inhibit formation of surface skin ulcers.

12 Claims, No Drawings

OTHER PUBLICATIONS

1972, Tissue Adhesives in Surgery, Chap. 1, Sec. III.

Matsumoto, Teruo, "Reactions of the Organism to Acrylate-Adhesives", pp. 436–444, 1972, Tissue Adhesives in Surgery.

Matsumoto, Teruo et al., "Tissue Adhesive and Wound Healing", pp. 266–271, Mar. 1969, Archives of Surgery, vol. 98.

Mizrahi, S. et al., "Use of Tissue Adhesives in the Repair of Lacerations in Children", pp. 312–313, Apr. 1988, Journal of Pediatric Surgery, vol. 23, No. 4.

Morton, R. J. et al., "The Use of Histoacryl Tissue Adhesive for the Primary Closure of Scalp Wounds", pp. 110–112, 1988, Archives of Emergency Medicine, vol. 5.

Ousterhout, D. K. et al., "Cutaneous Absorption of n-Alkyl-a-Cyanoacrylate", pp. 157–163, 1968, Journal of Biomedical Materials Research, vol. 2.

Pepper, D. C., "Kinetics and Mechanism of Zwitterionic Polymerization of Alkyl Cyanoacrylate", pp. 629–637, 1980, Polymer Journal, vol. 12, No. 9.

Pepper, David Charles et al., "Kinetics of Polymerization of Alkyl Cyanoacrylate by Tertiary Amines and phosphines", pp. 395–410, 1983, Makromol. Chem., vol. 184.

Ronis, Max L. et al., "Review of Cyanoacrylate Tissue Glues with Emphasis of Their Otorhinolaryngological Applications", pp. 210–213, Feb. 1984, Laryngoscope., vol. 94.

Saches, Michael Evan., "Enbucrylate as Carilage Adhesive in Augmentation Rhinoplasty", pp. 389–393, Jun. 1985, Archives of Otolaryngology, vol. 111.

Toriumi, Dean M. et al., "Histotoxicity of Cyanoacrylate Tissue Adhesives: A Comparative Study", pp. 546–550, Jun. 1990, Archives of Otolaryngology Head and Neck Surgery, vol. 116.

Tseng, Yin-Chao et al., "Modification of Synthesis and Investigation of Properties for 2-cyanoacrylate", pp. 73–79, Jan. 1990, Biomaterials, vol. 11.

Vinters, H. V. et al., "The Histotoxicity of Cyanoacrylate: A Selective Review", pp. 279–291, 1985, Neuroradiology, vol. 27.

Watson, David P., "Use of Cyanoacrylate Tissue Adhesive for Closing Facial Lacerations in Children", p. 1014, Oct. 1989, British Medical Journal, vol. 299.

METHODS FOR INHIBITING SKIN ULCERATION BY USE OF CYANOACRYLATE ADHESIVES

BACKGROUND OF THE INVENTION

1. Field of the Invention

This invention is directed to methods for inhibiting the formation of surface skin ulcers by using cyanoacrylate adhesives. The cyanoacrylate adhesive to be used can be stored in dispensers for single or repeated/intermittent use and can be applied to the skin by spraying, painting, etc. of the adhesive.

2. State of the Art

Cyanoacrylate adhesives have been suggested for a variety of adhesive purposes including glues and surgical adhesives. In particular, cyanoacrylate adhesives of formula I:

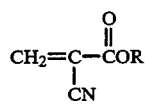

wherein R is an alkyl or other suitable substituents are disclosed in U.S. Pat. Nos. 3,527,224; 3,591,676; 3,667,472; 3,995,641; 4,035,334; and 4,650,826. Typically, when used as adhesives for living tissues, the R substituent is alkyl of from 2 to 6 carbon atoms and most often is butyl (e.g., n-butyl).

The suggested medical uses for cyanoacrylate adhesives include surgical environments wherein the cyanoacrylate adhesives are utilized, e.g., as an alternative to sutures or as a hemostat.

In contrast to such prior art uses of cyanoacrylate adhesives, this invention is directed to methods for inhibiting the formation of skin ulcers including, by way of example, decubitus ulcers (bedsores) and diabetic ulcers.

Decubitus ulcers arise from the deprivation of nutrients to the surface skin arising from prolonged pressure and are common in situations were the patient remains in a fixed position for prolonged periods (e.g., long term bed confinement). In particular, decubitus ulcer formation in nutrient deprived surface skin areas is facilitated by skin irritation due to moisture, friction, and shearing forces. Typically, decubitus ulcer formation is preceded by reddening of nutrient deprived skin which, with continued irritation, develops into the bedsore (i.e., a skin ulcer).

Diabetic ulcers are formed by deprivation of nutrients to the surface skin as a result of the diabetic condition including neuropathy, poor circulation in the patient, etc. In particular, diabetic ulcer formation in nutrient deprived surface skin areas is facilitated by skin irritation due to moisture, friction, and shearing forces. Typically, diabetic ulcer formation is preceded by reddening of nutrient deprived skin which, with continued irritation, develops into a skin ulcer.

In any event, once formed, skin ulceration is unsightly and is prone to infection. Therapies for treating skin ulcers have proven to be unsuccessful particularly in cases where the conditions causing skin ulceration remain unchanged. Accordingly, the health care industry has focused on measures to prevent the formation of skin ulcers. In the case of decubitus ulcers, conventional prophylactic methods include, by way of example, the use of sheepskin pads, the use of specialized beds, and the like. In the case of diabetic ulcers, conventional prophylactic methods include, by way of example, the use of pads in areas of nerve damage due to neuropathy (to prevent the patient from inflicting injuries to these areas due to lack of sensation), methods to enhance blood circulation in the patient, etc.

Notwithstanding such therapies, skin ulceration is a continuing problem with diabetic patients, bed ridden patients, and the like. Accordingly, there is an ongoing need to provide methods for inhibiting skin ulceration.

SUMMARY OF THE INVENTION

This invention is drawn to methods for inhibiting surface skin ulceration including, by way of example, decubitus ulcers (bedsores) and diabetic ulcers. The methods involve applying cyanoacrylate adhesive, particularly n-butyl cyanoacrylate adhesive, onto skin areas prone to surface skin ulceration so as to form a flexible, waterproof polymer layer over such skin areas. In turn, this polymer layer increases the skin integrity while reducing skin irritation to the underlying skin thereby inhibiting skin ulceration.

The methods described herein can be used by themselves to inhibit formation of surface skin ulcers but preferably are used in conjunction with existing regimens for inhibiting formation of surface skin ulcers.

Accordingly, in one of its method aspects, this invention is directed to a method for inhibiting the formation of surface skin ulcers which method comprises:
applying to a surface skin area prone to ulcer formation, a sufficient amount of a cyanoacrylate adhesive so as to cover said area; and
polymerizing the cyanoacrylate adhesive so as to form a flexible, waterproof, adhesive polymer coating which adheres to the area where the adhesive was applied,
wherein the cyanoacrylate, in monomeric form, is represented by formula I:

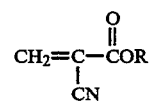

where R is selected from the group consisting of:
alkyl of 2 to 10 carbon atoms,
alkenyl of 2 to 10 carbon atoms,
cycloalkyl groups of from 5 to 8 carbon atoms,
phenyl,
2-ethoxyethyl,
3-methoxybutyl, and a substituent of the formula:

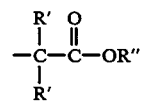

wherein each R' is independently selected from the group consisting of:
hydrogen and methyl, and R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably R is alkyl of from 2 to 10 carbon atoms and more preferably alkyl of from 2 to 6 carbon atoms. Even more preferably, R is butyl or pentyl and most preferably, R is n-butyl.

In a preferred embodiment, the cyanoacrylate is applied at a rate of at least 0.02 milliliter (ml), and preferably from about 0.02 to about 0.5 ml, of cyanoacrylate adhesive per square centimeter of skin which is to be covered.

In another preferred embodiment, the cyanoacrylate adhesive to be applied to the skin has a viscosity of from greater than 0 to about 100 centipoise at 20° C. More preferably, the cyanoacrylate adhesive is in monomeric form and has a viscosity of from greater than 0 to about 20 centipoise at 20° C.

As used herein, the following terms have the following meanings:

The term "cyanoacrylate adhesive" refers to adhesive formulations based on cyanoacrylate monomers of formula I:

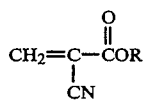

where R is selected from the group consisting of alkyl of 2 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula:

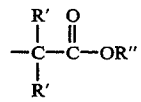

where each R' is independently selected from the group consisting of hydrogen and methyl and R" is selected from the group consisting of alkyl of from 1 to 6 carbon atoms; alkenyl of from 2 to 6 carbon atoms; alkynyl of from 2 to 6 carbon atoms; cycloalkyl of from 3 to 8 carbon atoms; aralkyl selected from the group consisting of benzyl, methylbenzyl and phenylethyl; phenyl; and phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl or pentyl and most preferably, R is n-butyl.

These cyanoacrylate adhesives are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

A preferred cyanoacrylate adhesive for use in the invention is n-butyl-2-cyanoacrylate.

The cyanoacrylate adhesives described herein rapidly polymerize in the presence of water vapor or tissue protein, and the n-butyl-cyanoacrylate is capable of bonding human skin tissue without causing histoxicity or cytotoxicity.

DETAILED DESCRIPTION OF THE PREFERRED EMBODIMENTS

This invention relates to cyanoacrylate adhesives which are useful for inhibiting formation of surface skin ulcers. The cyanoacrylate adhesive which is applied to surface skin areas prone to ulcer formation can be monomeric or partially polymeric. In general, partially polymerized cyanoacrylate adhesives are liquid polymers having a higher viscosity than that of the corresponding monomer and, therefore, are better suited for those applications which are intended to be specific for a particular skin area. In other words, less viscous materials are more likely to "run" (i.e., flow) into areas where application was not intended.

The cyanoacrylate adhesives used herein preferably have a viscosity of from greater than 0 to about 100 centipoise and more preferably from greater than 0 to about 20 centipoise at 20° C. The specific viscosity of the formulation depends on the amount and degree of partially polymerized cyanoacrylate adhesive employed. Such factors are readily ascertainable by the skilled artisan. For example, methods for preparing partially polymerized cyanoacrylate adhesives are disclosed, for example, by Rabinowitz, U.S. Pat. No. 3,527,224 which is incorporated herein by reference in its entirety.

Monomeric forms of cyanoacrylate adhesives are often preferred where application is to be made to a large surface area. This preference results from the fact that those forms are less viscous and, accordingly, will permit more facile large surface area application. Mixtures of monomeric forms of cyanoacrylate adhesive and partially polymerized forms of cyanoacrylate adhesive can also be used to prepare a formulation having intermediate viscosities.

For purposes of this invention, monomeric or partially polymerized n-butyl-2-cyanoacrylate is a particularly preferred adhesive and is capable of effectively bonding human skin tissue without causing histoxicity or cytotoxicity.

Upon contact with skin moisture and tissue protein, the cyanoacrylate adhesives will polymerize or, in the case of partially polymerized cyanoacrylate adhesives, will further polymerize, at ambient conditions (skin temperature) over about 10 to 60 seconds to provide a solid layer which forms over and strongly adheres to the surface of the skin. The resulting adhesive polymer layer or coating is flexible and waterproof thereby forming a protective layer which increases underlying skin integrity and reduces irritation to the surface skin area arising from shearing forces, moisture, friction, etc. In turn, increases in skin integrity and reduction in irritation inhibit formation of surface skin ulcers.

Surface skin areas prone to ulcer formation are readily identifiable to the skilled medical care provider. In a preferred embodiment, such skin areas are identified as areas of nutrient deprived and irritated skin. This latter characteristic is identified by reddening of the nutrient deprived skin. Reddening of nutrient deprived skin is viewed by the medical care provider as a likely point of skin ulceration.

The cyanoacrylate adhesive is applied to provide an effectively thick coating over the human skin tissue prone to surface ulcer formation. Generally, the cyanoacrylate adhesive provides an adhesive coating over the entire skin area prone to surface skin ulceration which, when set, is waterproof and satisfactorily flexible and adherent to the tissue without peeling or cracking. Preferably, the adhesive coating has a thickness of less than about 0.5 millimeter (mm), and more preferably the coating has a thickness of less than about 0.3 mm. In a particularly preferred embodiment, the thickness of the adhesive coating is from about 0.1 millimeter to about 0.5 millimeter and even more preferably from about 0.1 millimeter to about 0.3 millimeter.

The adhesive coating can be formed by applying at least about 0.02 ml of cyanoacrylate adhesive per square centimeter of skin and more preferably from about 0.02 to about 0.5 ml of cyanoacrylate adhesive per square centimeter of skin and even more preferably from about 0.02 to about 0.05 ml of cyanoacrylate adhesive per square centimeter of skin.

FORMULATIONS

The cyanoacrylate adhesive formulations employed herein generally comprise monomeric and/or partially polymerized compounds of formula I described above and are sometimes referred to herein as simply cyanoacrylate adhesives. These formulations are liquid in nature and, upon contact with surface skin proteins and moisture, will polymerize to provide a solid film or layer over the skin surface.

The formulations may additionally contain one or more optional additives such as colorants, perfumes, anti-diffusion agents, modifying agents and stabilizers. In practice, each of these optional additives should be both miscible and compatible with the cyanoacrylate adhesive. Compatible additives are those that do not prevent the use of the cyanoacrylate adhesives for their intended use.

In general, colorants are added so that the polymerized film will contain a discrete and discernable color. Perfumes are added to provide a pleasant smell to the formulation. Stabilizers are added to minimize in situ polymerization in containers during storage. Each of these additives is conventional. For example, suitable stabilizers are disclosed in U.S. Pat. No. 4,650,826 the disclosure of which is incorporated herein by reference in its entirety.

The amount of each of these optional additives employed in the cyanoacrylate adhesive is an amount necessary to achieve the desired effect.

The formulation is generally stored in an applicator for use in a single dose application or for use in repeated applications. Single dose applicators include those having breakable or removable seals that prevent moisture, including atmospheric moisture, from contacting the formulation and causing in situ polymerization.

For repeated and intermittent usage, minimal exposure to atmospheric moisture is required. This can be achieved by devices having very narrow outlets and low initial dead space. One applicator for such repeated intermittent use is described in U.S. Pat. No. 4,958,748 which is incorporated herein by reference.

Another applicator comprises a conventional spray applicator wherein the cyanoacrylate adhesive is sprayed onto the surface skin area prone to ulceration. The spray rate of the applicator can be controlled so that application of a metered quantity of adhesive per unit area of skin surface over a set period of time is controlled.

Still another applicator comprises a brush or solid paddle applicator wherein the cyanoacrylate adhesive is "painted" onto the surface skin area prone to skin ulceration.

A preferred applicator for repeated and intermittent usage is an applicator suitable for the non-sterile storage and metered dispersement of a cyanoacrylate adhesive after opening of the applicator wherein the applicator is characterized as having a resealable opening of no more than about 0.25 square inch (1.613 square centimeters) so as to permit the metered dispersement of the adhesive from the applicator and which is capable of multiple administrations of the adhesive and is further characterized as having resealing means such as a cap which either tightly mates with the applicator or which screws onto the applicator.

Preferably, the opening of the applicator is about 0.001 to about 0.10 square inch (about 0.00645 to about 0.645 square centimeters).

In another preferred embodiment, the walls of the applicator are made of a pliable material, so that upon application of pressure onto the walls, the walls depress sufficiently to force the adhesive contained in the applicator through the opening. Preferably, the applicator is manufactured with its opening covered by a metal foil or other similar construction which closes this opening until the device is ready for use. The opening is then reinstated by use of a pin or similar device which punctures the covering.

In applicators suitable for repeated intermittent uses, the cyanoacrylate adhesive is stored at ambient conditions and is selected to be bacteriostatic. See, for example, Rabinowitz et al., U.S. Pat. No. 3,527,224. When the selected adhesive is bacteriostatic, prolonged storage at ambient conditions can be achieved without regard to the sterility of the formulation.

METHODOLOGY

The above-described formulations are applied to surface skin areas prone to ulceration under conditions suitable for polymerizing the adhesive so as to form a protective coating. In general, sufficient amounts of cyanoacrylate adhesive are employed to cover (i.e., coat) the entire surface skin area prone to ulceration (e.g., the entire reddened area in nutrient deprived skin). The coating is preferably extended by at least about 1 centimeter and preferably by at least about 5 centimeters beyond the surface skin area prone to ulceration (e.g., beyond the reddened area described above).

The adhesive polymer coating should be maintained in a unbroken manner over the entire skin area prone to ulceration. This can be assured by careful application of the adhesive onto the skin. However, in a preferred embodiment, after the initial layer of adhesive has cured to provide for an adhesive polymer coating, a second, preferably thinner, layer is applied over the adhesive polymer coating. Additional amounts of cyanoacrylate adhesive can be applied as needed to maintain an unbroken callous like covering over the ulcer prone surface skin areas.

Sufficient cyanoacrylate adhesive is preferably employed to form a coating of less than about 0.5 mm thick and more preferably at least about 0.1 mm thick. Such coatings can be formed by applying at least about 0.02 ml of cyanoacrylate adhesive per square centimeter of skin surface area.

The amount of cyanoacrylate adhesive applied onto the skin surface area can be controlled by the amount of adhesive packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is particularly advantageous because it dispenses the adhesive in a controlled drop wise manner. Other methods for the controlled dispersement of the cyanoacrylate adhesive are as described above including, by way of example, a conventional spray applicator, a brush or solid paddle applicator, and the like.

Upon application of the cyanoacrylate adhesive, the surface skin moisture, tissue protein, and temperature are sufficient to initiate polymerization of the adhesive upon application. Thereafter, the skin surface is maintained under suitable conditions to allow polymerization to proceed to formation of an adhesive coating.

In general, the particular length of time required for polymerization will vary depending on factors such as the amount of adhesive applied, the temperature of the skin, the moisture content of the skin, the surface area of skin, and the like. However, in a preferred embodiment, polymerization is generally complete within about 10 to about 60 seconds while the skin is maintained at ambient conditions. During this period, the person to whom application of the cyanoacrylate adhesive has been made merely allows the adhesive to form a coating while minimizing any action to prevent the adhesive from being dislodged from that portion of the skin where it was applied or to adhere to unintended objects. Excess adhesive polymer can be removed with acetone (nail polish remover) which can be readily conducted except in the case where the adhesive polymer binds to a sensitive skin part (e.g., the eye lids) where it should be removed by a health care professional.

After the adhesive coating has formed, the coating strongly adheres to the skin, is flexible and waterproof, thereby forming a protective coating which enhances the integrity of the underlying skin and protects the skin from further irritation thereby retarding or inhibiting surface skin ulceration.

In general, the coating will adhere to the skin for a period of about 2–3 days after which time it sloughs off. Additional applications can be made if desired.

Because the cyanoacrylate adhesive polymer coating is waterproof, the patient is not prevented from bathing and other activities involving exposure to water during the period the adhesive layer protects this skin area.

The following examples illustrate certain embodiments of the invention but is not meant to limit the scope of the claims in any way.

EXAMPLES

Example 1

A cyanoacrylate adhesive formulation is prepared in monomeric form using n-butyl α-cyanoacrylate and which contains a colorant to readily ascertain where the formulation has been applied. The formulation is applied onto an approximately 5 square centimeter nutrient deprived and irritated skin area prone to surface skin ulceration which, in this case, is prone to decubitus ulcer formation on the buttocks of a bed ridden human male patient as evidenced by reddening of this skin indicating irritation. The formulation is applied at the rate of 0.1 milliliter per square centimeter of treated skin and, after application, the skin is maintained at ambient condition until a polymer coating forms in about 30 seconds. After the polymer coating has formed, preventive methods to inhibit decubitus ulcer formation in the patient, including, sheepskin pads, specialized beds, and the like, are continued.

In this regard, the application of the cyanoacrylate adhesive polymer layer to the skin area prone to decubitus ulcer formation in conjunction with other conventional therapies to prevent decubitus ulcer formation will reduce the rate of decubitus ulcer formation as compared to treatments involving conventional therapies without application of the adhesive polymer layer.

Example 2

A cyanoacrylate adhesive formulation is prepared in monomeric form using n-butyl α-cyanoacrylate and which contains a colorant to readily ascertain where the formulation has been applied. The formulation is applied onto an approximately 1 square centimeter nutrient deprived and irritated skin area prone to surface skin ulceration which, in this case, is prone to diabetic ulcer formation on the foot of a human female patient as evidenced by reddening of this skin indicating irritation. The formulation is applied at the rate of 0.1 milliliter per square centimeter of treated skin and, after application, the skin is maintained at ambient condition until a polymer coating forms in about 30 seconds. After the polymer coating has formed, preventive methods to inhibit diabetic ulceration in this patient, including, the use of pads, methods to enhance blood circulation in the patient, and the like, are continued.

In this regard, the application of the cyanoacrylate adhesive polymer layer to the skin area prone to diabetic ulceration in conjunction with other conventional therapies to inhibit diabetic ulceration will reduce the rate of diabetic ulceration as compared to treatments involving conventional therapies without application of the adhesive polymer layer.

From the foregoing description, various modifications and changes in the composition and method will occur to those skilled in the art. All such modifications coming within the scope of the appended claims are intended to be included therein.

What is claimed is:

1. A method for inhibiting the formation of surface skin ulcers in a patient which method comprises:
employing conventional prophylactic treatment on the patient to inhibit surface skin ulcer formation in conjunction with applying to a surface skin area prone to ulceration, wherein said area is not contiguous with a formed open pressure sore, a sufficient amount of a cyanoacrylate adhesive so as to cover said area; and
polymerizing the cyanoacrylate adhesive so as to form a flexible, waterproof, adhesive polymer coating which adheres to the area where the adhesive was applied,
wherein the cyanoacrylate, in monomeric form, is represented by the formula:

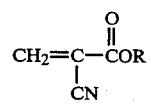

I where R is selected from the group consisting of:
alkyl of 2 to 10 carbon atoms,
alkenyl of 2 to 10 carbon atoms,
cycloalkyl groups of from 5 to 8 carbon atoms, phenyl,
2-ethoxyethyl,
3-methoxybutyl,
and a substituent of the formula:

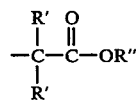

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and allfoxy of from 1 to 4 carbon atoms.

2. A method according to claim 1 wherein R is alkyl of from 2 to 6 carbon atoms.

3. A method according to claim 2 wherein R is butyl or pentyl.

4. A method according to claim 3 wherein R is n-butyl.

5. A method according to claim 1 wherein said adhesive is applied so as to provide at least 0.02 ml of cyanoacrylate adhesive per square centimeter of skin which is to be covered.

6. A method according to claim 5 wherein the cyanoacrylate adhesive is applied so as to provide from about 0.02 ml to about 0.5 ml per square centimeter of skin which is to be covered.

7. A method according to claim 6 wherein the cyanoacrylate adhesive is applied so as to provide from about 0.02 ml to about 0.05 ml per square centimeter of skin which is to be covered.

8. A method according to claim 1 wherein the cyanoacrylate adhesive has a viscosity of from greater than 0 to about 100 centipoise at 20° C.

9. A method according to claim 8 wherein the cyanoacrylate adhesive has a viscosity of from greater than 0 to about 20 centipoise at 20° C.

10. A method according to claim 1 wherein said ulcers are either decubitus ulcers or diabetic ulcers.

11. A method according to claim 10 wherein said ulcers are decubitus ulcers.

12. A method according to claim 11 wherein the surface skin ulcers are diabetic ulcers.

* * * * *